United States Patent [19]

Terry et al.

[11] 4,237,873
[45] Dec. 9, 1980

[54] CEREBRAL PALSY ARM AND HAND BRACE

[76] Inventors: Thomas E. Terry, 204 E. Athey R.R. #1, Farber, Mo. 63345; Laurance J. Hoyt, Sr., R.R. #2, Laddonia, Mo. 63352

[21] Appl. No.: 967,900

[22] Filed: Dec. 11, 1978

[51] Int. Cl.³ .............................................. A61F 5/01
[52] U.S. Cl. ........................................ 128/77; 128/88
[58] Field of Search ............... 128/77, 78, 80 R, 80 F, 128/80 G, 87 R, 88, 94; 3/1.1, 1.2; 272/132, 139; 248/118, 118.1

[56] References Cited

U.S. PATENT DOCUMENTS

| | | | |
|---|---|---|---|
| 649,237 | 5/1900 | Dyson | 128/88 |
| 1,639,815 | 8/1927 | Siebrandt | 128/88 |
| 2,362,383 | 11/1944 | Lendinara | 128/80 F |
| 2,498,115 | 2/1950 | Purgett | 128/80 R |
| 2,661,000 | 12/1953 | Gazeley et al. | 128/88 |
| 3,528,413 | 9/1970 | Aydt | 128/88 |
| 3,769,636 | 11/1973 | Friedman | 3/1.1 |
| 4,149,532 | 4/1979 | Terry et al. | 128/77 |

FOREIGN PATENT DOCUMENTS 508227 10/1920 France ................................ 128/80 C

OTHER PUBLICATIONS

*The Engineer*, Time-Life Books, New York, by Furnas, C. C., ©1966, pp. 162–163.

Primary Examiner—Robert W. Michell
Assistant Examiner—Arthur S. Rose
Attorney, Agent, or Firm—Thomas M. Scofield

[57] ABSTRACT

An arm and hand brace for persons afflicted with the neuro-muscular tremors of cerebral palsy; a bracing device framing the shoulders, upper arm, forearm and hand which, in application, damps and controls involuntary neuro-muscular spasms and permits the performance of controlled, willed actions of these members by cerebral palsy victims; an articulated frame comprised of a support, a train of linked arms, a sleeve clasping the hand, wrist and forearm, a series of double and single element joints and a piston-piston rod extension-retraction system, all for establishing and maintaining control of gross and fine arm and hand movements in the cerebral palsy patient.

7 Claims, 15 Drawing Figures

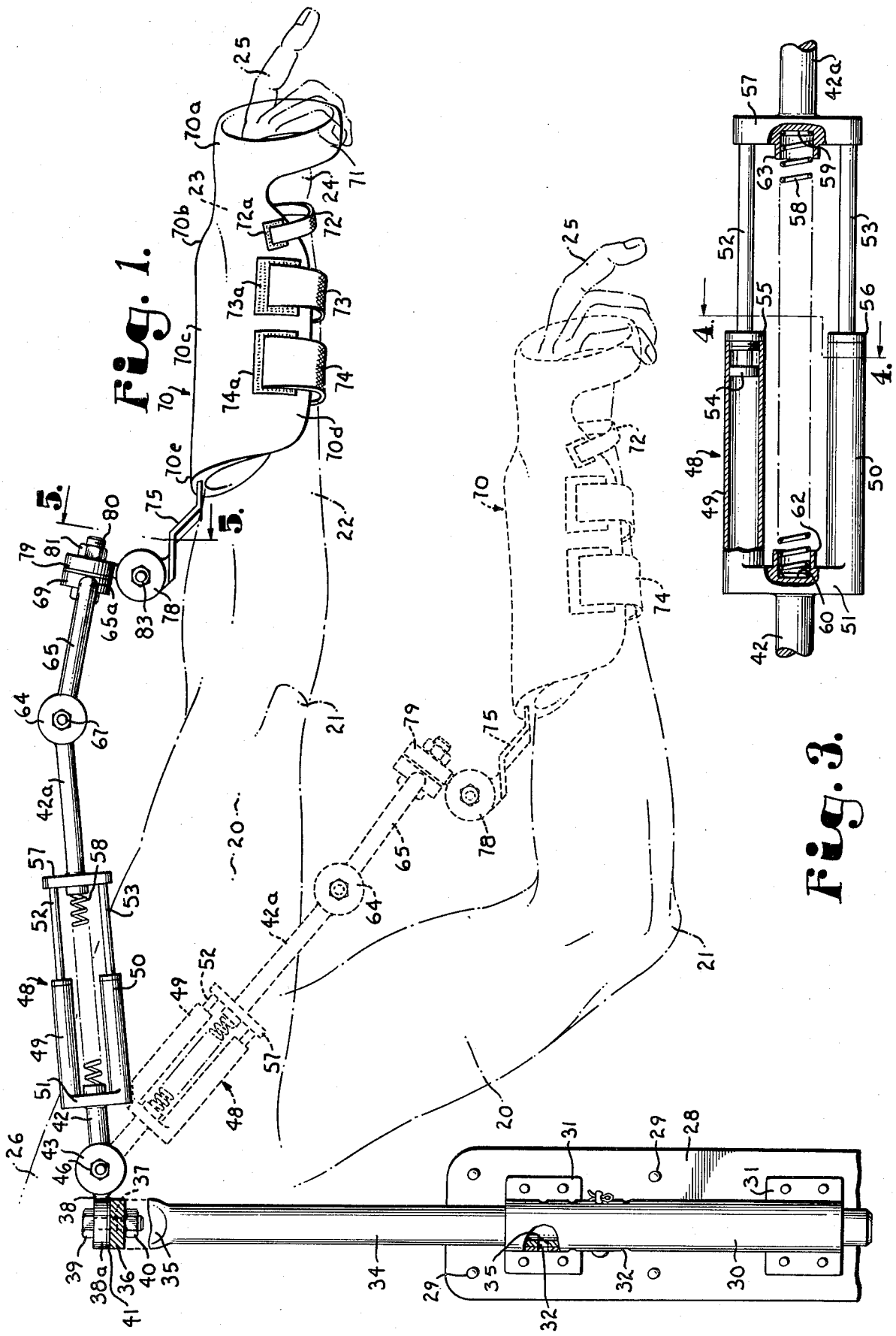

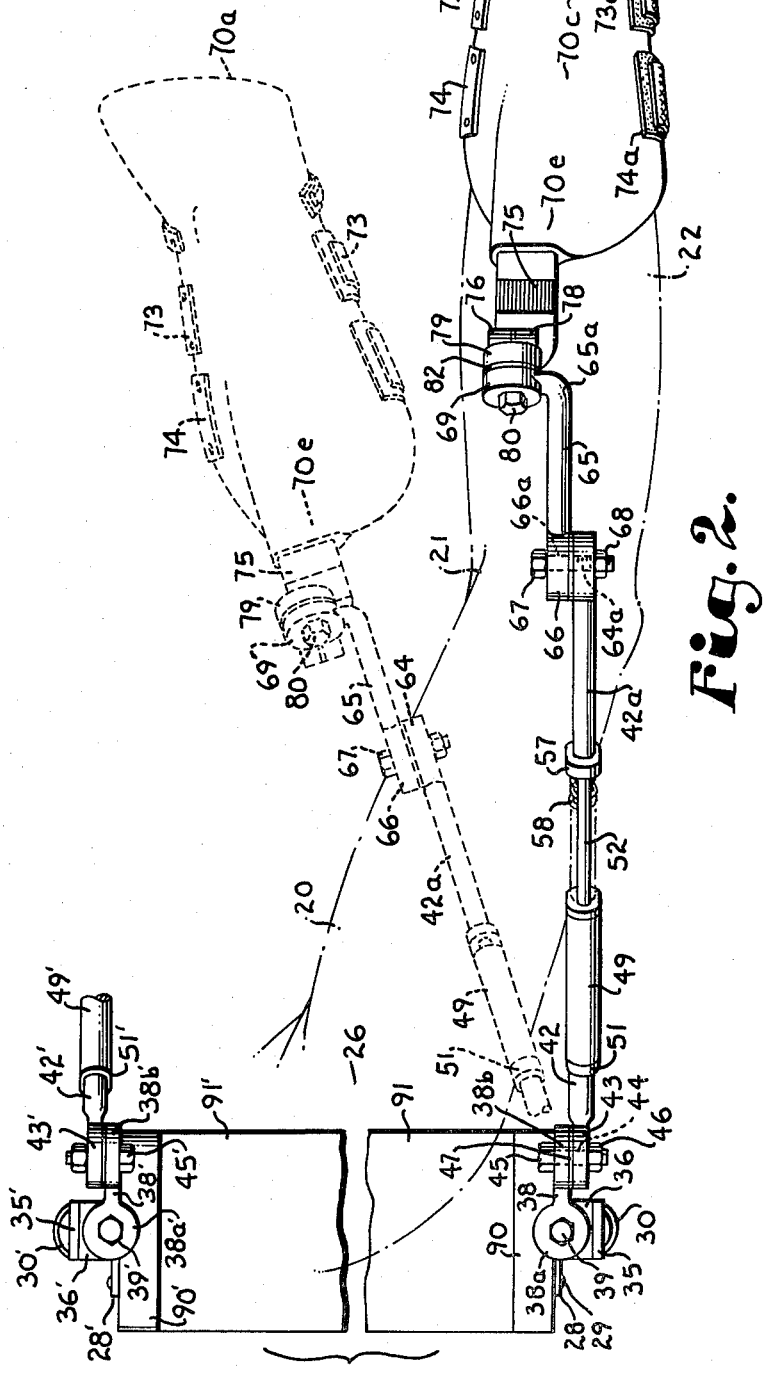
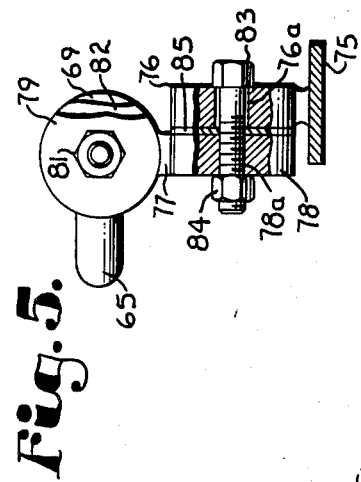
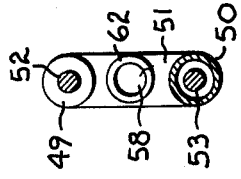

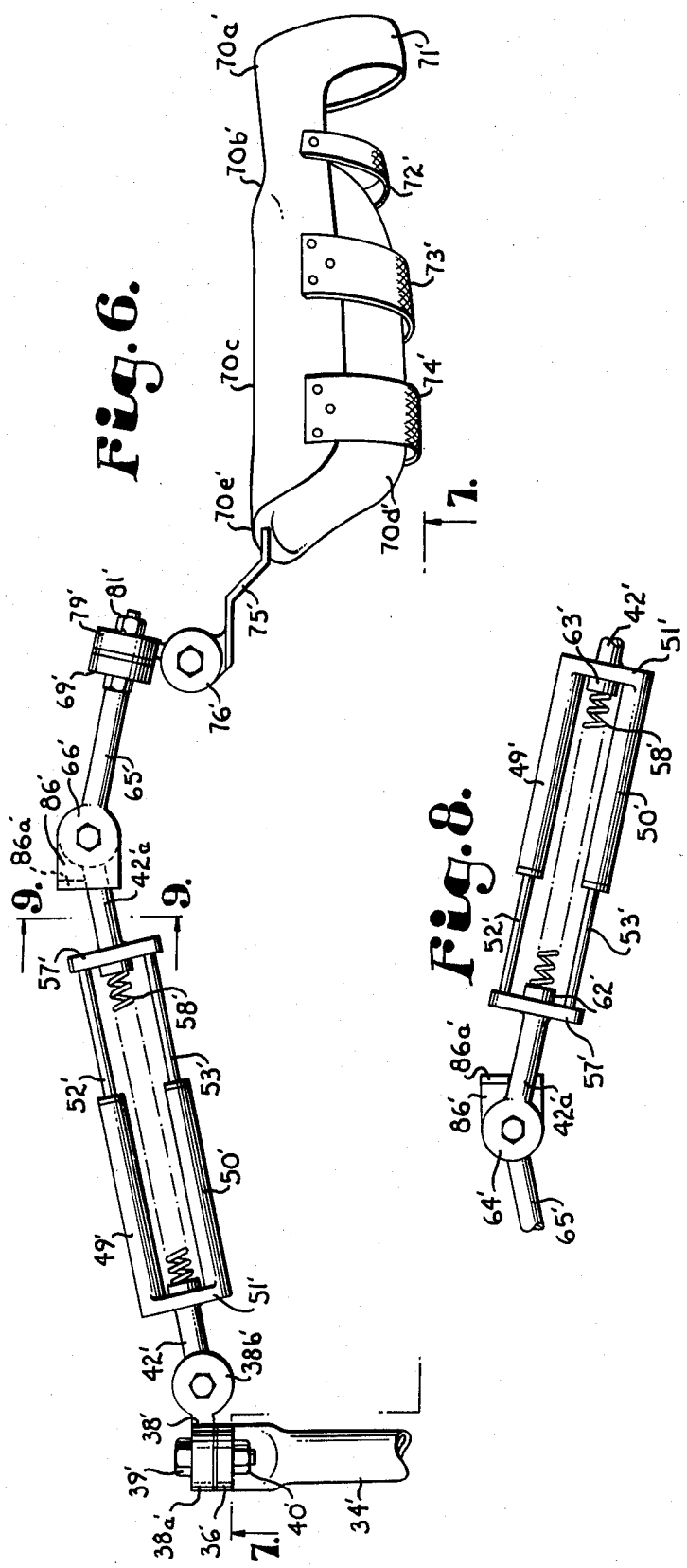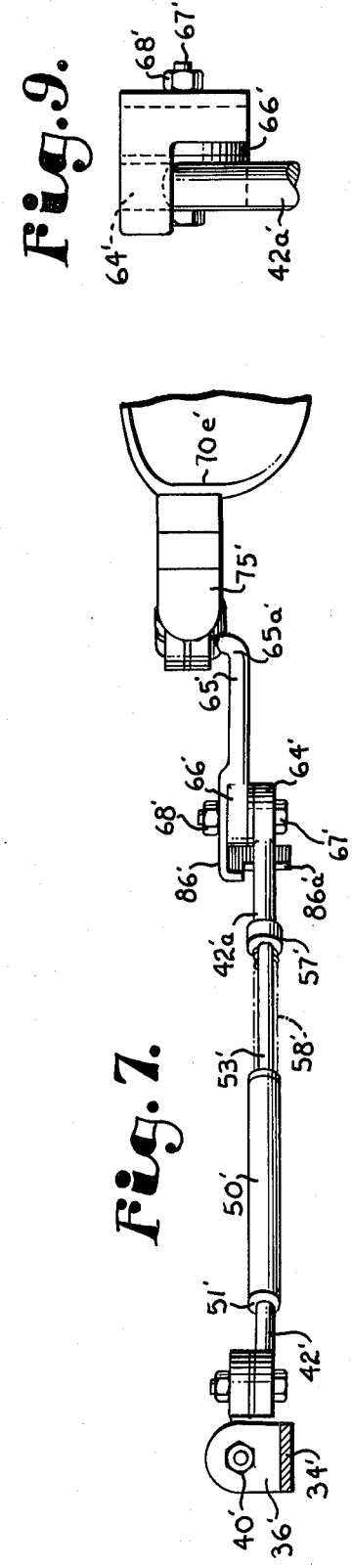

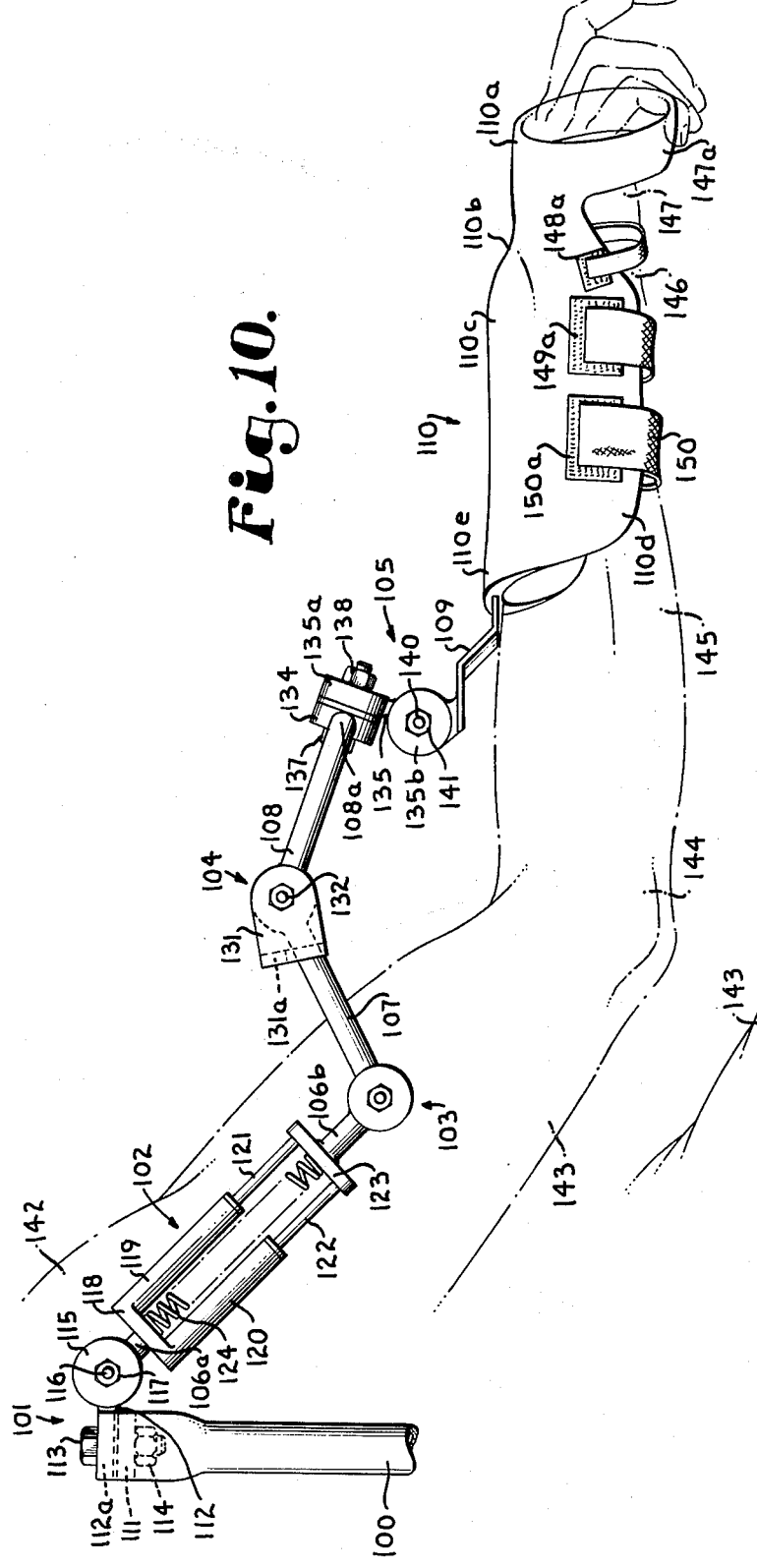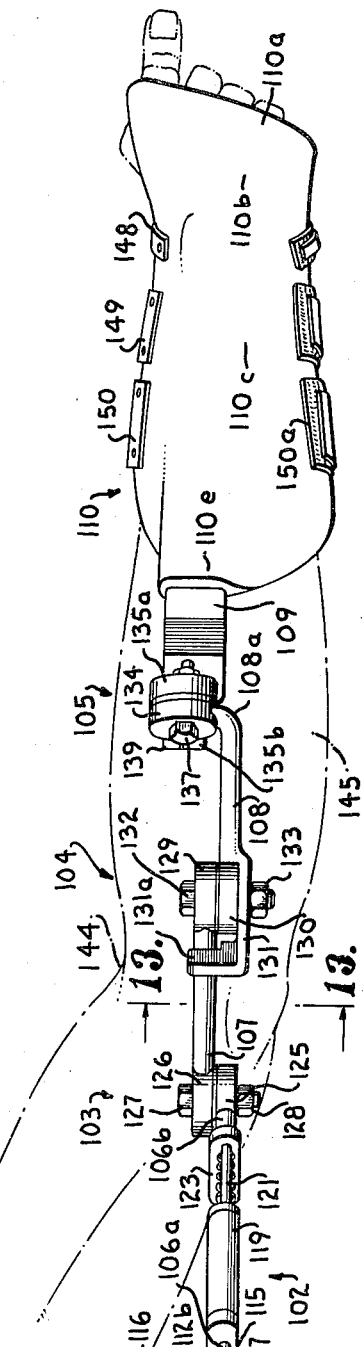

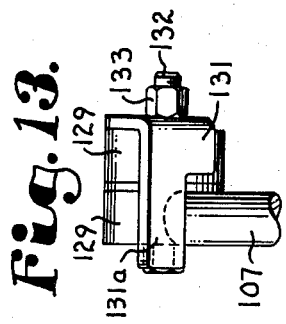
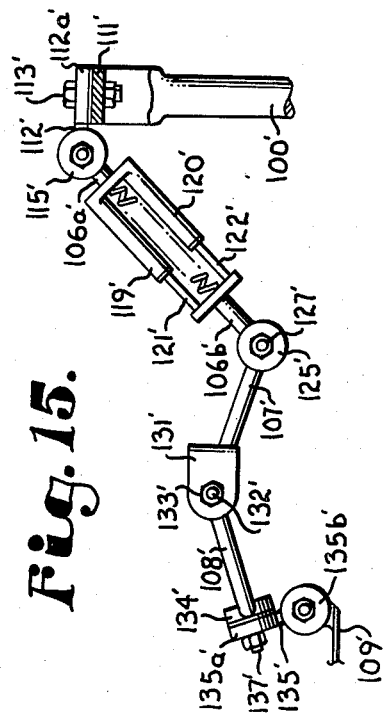
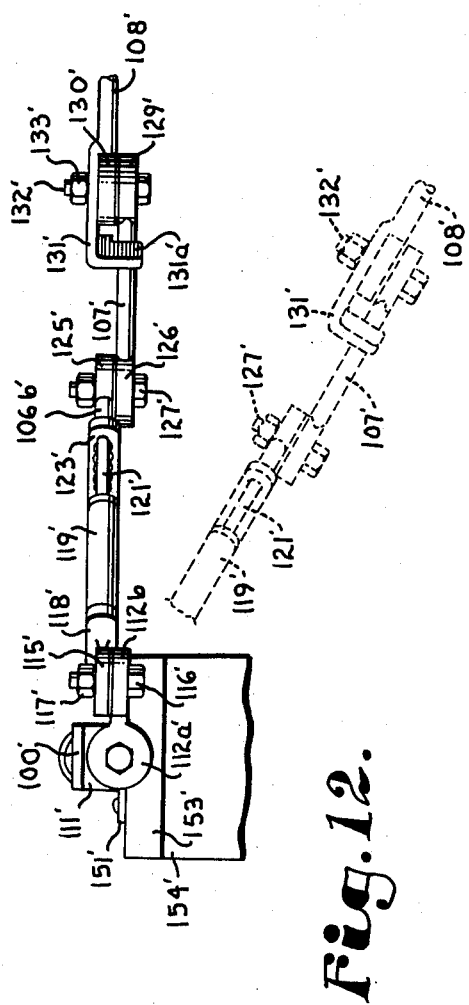
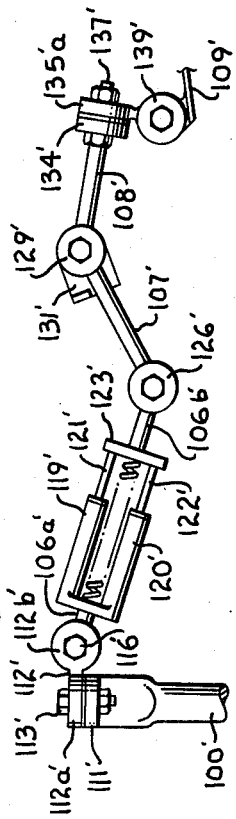

CEREBRAL PALSY ARM AND HAND BRACE

BACKGROUND OF THE INVENTION

The literature of cerebral palsy is voluminous. The instant invention is directed to certain specific problems arising out of certain manifestations of certain forms of cerebral palsy.

The latter is a condition primarily centered around paralysis, incoordination or weakness of the muscular system due to pathology of the motor control centers of the brain. Typically, it is a term covering motor disabilities due to nonprogressive brain pathology typically occurring in early life. With respect to causation, broad definitions speak of prenatal, natal and postnatal pathological processes having deleterious effects on the pyramidal, extra-pyramidal or cerebellar systems. With respect to a classification of types, approaches involve (a) pathology, (b) the presenting clinical syndromes and (c) the regions of the body affected.

Five types are generally recognized in cerebral palsy, with varying degrees and types of motor involvement: spastic, dyskinetic (including athethoid), ataxic, mixed and flaccid. The American Academy of Cerebral Palsy recognizes seven types: spastic, athetotic (tension, non-tension, dystonia and tremor athetosis), rigidity, ataxic, tremor, atonic and mixed. Speaking descriptively, the spastic type, comprising some 65% of the cerebral palsied, typically involves stiffness of musculature, with motions of the extremities made slowly and with great effort. Thus, when the afflicted person attempts to bend the joints, the opposing muscles contract, blocking the patient's efforts. In the athetoid type, typically comprising 30% of the afflicted, the individual moves his body or parts of his body even when he does not wish to. The body and extremities may be in constant motion. The individual may have difficulty in controlling and directing his movements. Phelps recognizes nine types of athetoids. These include rotary, dystonic, tremor-like, shudder-like, flail, non-tension, hemi-athetoid and emotional release athetosis.

In a classification based on neuromuscular characteristics, five types were distinguished, including spasticity, athetosis, tremor, rigidity and ataxia. With respect to the tremor syndrome, the muscles are typically normal in tone with no abnormal reflexes. The distinguishing characteristic is repetitive and rhythmic involuntary contractions of the flexor and extensor muscles. In the intentional sub-class, such are not present at rest and appear with voluntary or intended movement. In the non-intentional sub-class, such are present at rest and also continue with intended movement. Typically, these involuntary movements are fine and rhythmic, not gross and variable like the athetoid type. In the lower extremities, such tremors tend to throw the individual off balance. In the upper extremities, they interfere with hand skills and often may prevent development of writing skills and the like.

In therapy of cerebral palsy conditions, rests, body braces, special chairs and tables, corsets and other devices may be used to control those motions which use up much of the energy of cerebral palsied individuals. Motion training may also use such devices.

With respect to the philosophy of bracing and special equipment in treatment of cerebral palsy, the need arises from the disturbances of the neuromuscular function. There are differences of opinion with respect to the value of bracing and other special equipment in treatment. Some physicians value and some contraindicate. The purpose of use of such special equipment is to provide needed support, aid in control of involuntary movements, prevent or correct deformities and combinations of these.

In the literature, it is recognized that bracing and special equipment applied to the upper extremities is much less common. It is typically not needed for erect posture of the individual. To correct and prevent deformities of the upper extremities is very difficult. Many physicians consider it impractical to brace the shoulder and elbow joints. In such use, bracing of spastic hands is the most common type in order to counteract flexion deformities.

The previous ideas have been abstracted from the works of Allen, R. M. et al "Psychological Evaluation of the Cerebral Palsied Person" and McDonald, E. T. et al "Cerebral Palsy".

In Keats, Sidney "Cerebral Palsy", 1965, C. C. Thomas, Springfield, Illinois, under Chapter V Modalities of Treatment, Subsection 6 Bracing, Page 236, there is first discussed foot, leg and back braces, particularly directed toward treatment of athetoid syndromes. Thereafter occurs a discussion of problems and efforts to control involuntary arm movement, such being devised according to the individual problem. Mentioned are spoon splints to prevent wrist flexion (which may extend to the forearm), hand sandwich braces to aid in controlling wrist and hand extension and forearm splint braces which may go above the elbow joint to maintain full or mid-supinated forearm position. Such may permit flexion and extension at the elbow joint with the forearm and hand in position of mid-supination. It also may have a bar to prevent hand rotation through the wrist.

In Cruikshank, William N. (editor) "Cerebral Palsy, Its Individual And Community Problems", 1966, Syracuse University Press, Part C, Therapy and Education, Section VIII, Physical Therapy (Ester E. Snell), bracing is discussed at page 412 et seq. Such is discussed for support, the correction of deformities and control of extra motion. Materials are given typically as steel, aluminum and plastic. Parts mentioned are uprights, crossbands, joints, stops, cuffs, pelvic bands, gluteal pads, knee caps and knee pads. In joint classification, there are mentioned simple, box, ball bearing and spring joints.

Throughout these works, and in many others related, there runs the theme of non-intellectually impaired and often superiorly motivated individuals who are yet incapacitated to a greater or lesser degree (often greater) by their damaged motor nervous systems. Additionally, the frustration of inability to accurately and, with control, perform known, projected and willed acts for such people need not be described. It is this problem of furnishing specific means by which these physically handicapped individuals may capture or recapture neuromuscular function permitting them to do fine, controlled, willed work towards which this invention and application are directed. The purpose is to provide mechanical means by which the gross and fine action and function of the entire arm and hand complex may be stabilized and controlled, despite the presence of the previously incapacitating and disabling tremors. With this recovery or capturing of these crucial actions and functions, the afflicted individual is able to grasp an aspect of himself previously denied of the highest importance.

Additionally, therapy of these conditions is enabled to enter new realms previously denied it.

THE PRIOR ART

Applicant is aware of the following prior art patents directed to arm and hand splints and braces and joint constructions:

Maddox U.S. Pat. No. 1,340,630 "Arm Abduction Splint", issued May 18, 1920;

Lendinara U.S. Pat. No. 2,362,383 "Flexible Joints", issued Nov. 7, 1944;

Whitelaw U.S. Pat. No. 2,832,334 "Therapeutic Device . . . ", issued Apr. 29, 1958;

Keropian U.S. Pat. No. 3,707,963 "Articulated Hand Brace", issued Jan. 2, 1973.

Reference is also made to the Life Science Library work "The Engineer", by C. C. Furnas, et al, 1968 revision, Time-Life Books, New York City, New York, pages 162 and 163 with respect to the "Man Amplifier".

BRIEF DESCRIPTION OF THE INVENTION

Spasticity or spastic paralysis is generally regarded as a form of cerebral palsy. Cerebral palsy itself is broadly regarded as any non-progressive motor disorder typically caused by brain damage incurred during individual development. Thus, cerebral palsy is a non-specific term and typically includes many kinds of brain damage from various causes. Few authorities agree on the disorders to include.

In many forms or degrees of the neuro-motor disorders labelled spasticity and spastic paralysis, willed movements of the entire arm, the upper arm, the forearm, hands and fingers are possible and feasible, but the effectiveness of such willed movements is vitiated and overshadowed by the presence of intermittent or continuous tremors or tremoring in the limbs and hands. What, then, is needed is a suitable brace or device which will clasp an arm or both arms in such a manner that the unwilled and undesired neuromuscular spasms and tremors will be damped and controlled, but the willed movements of the various arm and hand elements, gross and fine, not prevented.

The instant improved device has had remarkable success in stabilizing the said arm and hand tremors of individuals suffering from spasticity and spastic paralysis, permitting them to feed themselves, typewrite, write, in short control their gross and fine arm and hand movements, specifically including:

(1) Complete shoulder articulation (up, down, sideways, arcuate, etc.);

(2) Flex and extend the forearm with respect to the upper arm at the elbow;

(3) Pronate and supinate the forearm; and (4) Brace the hand across the palm thereof in order to permit fine finger movements and actions.

One device for one arm or two devices for both arms may be connected to the back of a chair, to a wheel chair frame, or even to a back plate strapped to the individuals themselves to provide mobile aid.

The instant device typically includes the following elements, working from the attachment on the chair, wheel chair, standing frame or back plate:

(1) A hollow sleeve adapted to removably receive and removably lock therewithin (by pins through the sleeve):

(2) The normally vertical shaft received within the said sleeve and pinned therein against rotational movement and vertical movement;

(3) A forearm clasping and hand encircling sleeve;

(4) A train of arms, a piston-piston rod unit received in one of the arm lengths and articulating joints between the arm lengths, comprising:

(a) A double element joint adjacent the shoulder of the user;

(b) Within the arm length next adjacent the latter mentioned double element joint, a piston-piston rod construction having a spring loading;

(c) A single element inboard joint either between the shoulder and elbow or adjacent the elbow;

(d) Optionally, a single element joint with an arm limitation (against excessive elbow extension) at the elbow; and (e) A double element joint just over the forearm past the elbow closely adjacent the inboard end of the sleeve.

A double element joint comprises two closely adjacent, right angle oriented sets of pinned, sliding, circular plates permitting multi-dimensional and multi-planar movement. A single element joint is one such set with movement limited to one plane.

The upper double element joint next to the vertical shaft at the shoulder permits shoulder articulation. The piston-piston rod assembly and the one or two intermediate single element joints, in combination and cooperation, permit flexion and extension of the forearm with respect to the elbow. The lower double element joint permits pronation and supination of the forearm with respect to the elbow joint.

There is provided a frictional loading at each joint element which operates, jointly and severally, to damp the muscle spasms and neuro-muscular oscillations which are involuntary and unwilled. Variable resistance is provided at each joint element so that the entire train of joint elements is uniquely variably adjustable for a given individual's problems. The frictional engagement is accomplished by tightening down the bolt engagement of each of the joint element face sets, with a threaded engagement and lock nut arrangement at each such joint element.

OBJECTS OF THE INVENTION

One object of this invention is to improve over the device of my currently pending application Ser. No. 754,536, filed Dec. 27, 1976, for "Cerebral Palsy Arm And Hand Brace". The specific improvement involves the insertion of a piston-piston rod assembly with a spring load in the upper arm lengths adjacent the shoulder with or without the replacement of one of the single element joints in order to facilitate the raising and lowering of the forearm and hand clasping sleeve, thus easing and facilitating the basic arm flexion at the elbow joint.

A first and primary object of the invention is to provide a device which will aid in stabilizing or, in fact, effectively so control or limit the arm tremors of spastic paralytics that they are able to feed themselves, move their arms and hands in a controlled manner, typewrite, write, in short, control their gross and fine arm movements.

Another object to the invention is to provide such an improved device for stabilizing the arm tremors of spastic paralytics which enables the afflicted person to perform:

(1) Complete shoulder articulation (up, down, sidewise, arcuate, etc.);

(2) Flexion and extension of the forearm with respect to the upper arm at the elbow; and (3) Pronation and supination of the forearm. In addition, means are provided which enable the performance of fine finger movement in willed action and control.

Still another object of the invention is to provide an arm outlining frame which may be employed with one or both arms by an individual suffering from the uncontrollable tremors of spastic paralysis (one frame for each arm), which frame or frames articulate(s) in such manner as to permit all of the normal gross and fine upper arm, forearm and hand movements, yet simultaneously provides, with respect to each movement or pattern thereof, continuous, graded resistance at all times, so that, continuously, the entire arm structure of the afflicted individual is caged or controlled against the uncontrollable tremors or movements of the disease, yet may, by willed action, force gross and/or fine action through and against the frame.

Another object of the invention is to provide such an arm framing and engaging device of the character described which may be mounted on a vertical standing frame (for standup use), alternatively may be removably secured to a chair back (for sitting use) or, yet alternatively, may be secured to a frame strapped to the body of the user (for mobile use).

Yet another object of the invention is to provide such a device, of the character described, which device is extremely strong and rugged in use, of long life despite continuous and hard use, dependable in action and, finally, of a relative minimum of cost to fabricate. Yet further, all of the parts of the device are readily available for adjustment, replacement or repair.

Still another and further object of the invention is to provide an arm engaging and framing device of the character described, wherein a multiplicity of doubly and singly jointed arms connect a vertical post and a forearm engaging sleeve, there being a frictional loading at each joint element which operates to damp the muscle spasms and neuro-muscular oscillations of the afflicted individual, the frictional loading and engagement at each joint element being individually variable and adjustable. Yet further, there is provided a piston-piston rod assembly having a spring loading which facilitates and aids in flexion and extension of the forearm with respect to the upper arm at the elbow joint.

Still another object of the invention is to provide a multiply jointed, articulated frame for use in a device of the character described wherein, as mentioned, there is a frictional loading at each joint element. Despite this fact and despite the fact that the device will typically be used for many years with all the joints being exercised, in every way possible, the joint element construction is such that no substantial wear or deterioration of any of the joint elements will occur over the years and the infinite variability of adjustment of each joint element will not deteriorate from use or aging. Yet further, the piston-piston rod assembly and its spring loading, are of simple, rugged construction also of long life without excessive wear or malfunction.

Yet another object of the invention is to provide such a device, frame and articulation thereof, as well as structural configuration, wherein an absolute minimum of maintenance and repair will be required over the years and such daily or periodic adjustment of joint frictional loadings as may be required is readily and easily made, without any difficulty and with constant full access to every joint element.

Other and further objects will appear in the course of the following description of the invention.

In the drawings, which form a part of the instant specification and are to be read in conjunction therewith, embodiments of the invention are shown and, in the various views, like numerals are employed to indicate like parts.

DESCRIPTION OF THE DRAWINGS

FIGS. 1-9, inclusive show a first form of the subject improved neuromuscular stabilizing device for the human arm and hand.

FIG. 1 is a side view showing the subject stabilizing device as applied to the right arm of the user. In full lines, in the upper portion of the view, the user's right arm is shown essentially fully extended and slightly pronated so the palm is down. In the dotted line showing of FIG. 1 below the full line showing, the user's right arm is shown somewhat flexed toward himself, with substantially the same degree of pronation. In the lower left hand corner of the view of FIG. 1, the mounting for the device is seen.

FIG. 2 is a top view of the apparatus of FIG. 1 with the illustrated portions of FIG. 2 in full and dotted line showings corresponding to the full and dotted line showings of FIG. 1. In the upper left hand portion of FIG. 2, the mounting for a left arm device is fragmentarily shown.

FIG. 3 is an enlarged, side, partly sectional view of the piston-piston rod extension-retraction apparatus seen in the upper left hand portion of the view of FIG. 1.

FIG. 4 is a view taken along the lines 4—4 of FIG. 3 in the direction of the arrows.

FIG. 5 is a view taken along the lines 5—5 of FIG. 1 in the direction of the arrows.

FIG. 6 is a side view of the left arm device of FIG. 2. The construction shown differs from the right arm device in that a motion limiting structure is provided at the elbow joint and the extension-retraction device is of greater length than that seen in FIGS. 1 and 2.

FIG. 7 is an underside view of the left hand side of the structure of FIG. 6.

FIG. 8 is a fragmentary view of the opposite side of the elbow joint and sleeve connection from that seen in FIG. 6.

FIG. 9 is a view taken along the line 9—9 of FIG. 6 in the direction of the arrows.

FIGS. 10-15, inclusive are directed to a modified form of the subject neuromuscular stabilizing device for the human arm and hand.

FIG. 10 is a side view of the modified form of neuromuscular stabilizing device showing such applied to the right arm of the user with the user's right arm at a degree of extension thereof intermediate the extension positions shown in full and dotted lines in FIG. 1. The forearm is slightly pronated so that the palm of the hand faces downwardly in the view.

FIG. 11 is a top plan view of the device of FIG. 10.

FIG. 12 is a fragmentary top plan view of the modified form of device of FIGS. 10 and 11, fragmentarily showing, in full lines, the left arm unit of the device extended to the same position as the device of the showing in FIG. 11. In dotted lines, the arm frame is shown moved downwardly and to the left in the view.

FIG. 13 is a view taken along the lines 13—13 of FIG. 11 in the direction of the arrows.

FIG. 14 is a fragmentary side view of the left arm stabilizing device of FIG. 12 taken, in the view of FIG. 12, from the lower portion of the view looking upwardly (inside of the frame looking outwardly).

FIG. 15 is a fragmentary side view of the left arm stabilizing device of FIGS. 12 and 14, the view, with respect to FIG. 12, taken from above, looking downwardly in the view.

STRUCTURE & FUNCTION

Turning to the drawings, the first construction will now be described in detail and its structure and function set forth. In FIGS. 1, 2 and 3 there is seen the upper arm 20, the elbow joint 21, the forearm 22, the wrist 23 and hand 24 with fingers 25 of the user of the device. The shoulder portion 26 of the individual may also be seen in the views.

The fundamental base or support construction mounting the entire apparatus to be described is best seen in the lower left hand corner of FIG. 1. This comprises a plate 28, which may be attached (typically, but not limiting) to the back of a chair, to a wheel chair frame, or even to a back plate strapped to the individual himself. Suitable bolt, screw or rivet holes 29 are shown on plate 28 for conventional attachment to an underlying support construction. Yet another method of mounting the apparatus to be described and plate 28 supporting same could comprise vertical beams or a vertical frame fixed adjacent to a place of work, such as a work bench or the like, such beams mounted on moveable stands or fixed to a floor.

A hollow cylindrical sleeve 30 is fixedly attached to or gripped upon plate 28 by conventional means such as brackets 31. The orientation of plate or plates 28 (two such plates would be employed, one on each side of the individual, where both arms of the individual were to be coupled with the subject devices) is preferably, but not necessarily, substantially vertical so that the orientation of hollow cylindrical sleeve 30 is also preferably (not necessarily) substantially vertical. Vertically spaced sets of opposed openings 32 are provided in sleeve 30 to receive therethrough one or more pins 33. Pins 33 serve to fix the vertical and rotational position of cylindrical tube or shaft 34 which is removeably receivable within sleeve 30. The shaft 34 has one or more sets of oppositely matched, opposed perforations or openings 35 in the wall thereof adapted to align with openings 32 in sleeve 30. Both sleeve 30 and shaft 34 may be square, hexagonal, etc. in transverse horizontal section (in the view of FIG. 1), if desired, but circular section is simplest and easiest. Height adjustment of the top of shaft 34 with respect to plate 28 is provided by the multiplicity of openings 32 in sleeve 30, which may be positioned along the entire length of the sleeve 30, as well as the many openings 35 in shaft 34.

The upper portion of hollow shaft 34 is flattened as at 35 and a right angle, normally horizontal, rounded end flange 36 having a threaded opening 37 therethrough is provided at the top of shaft 34. A short, double joint member 38 has two essentially circular, opposed, right angle oriented portions 38a and 38b thereon. Portion 38a overlies flange 36 and is coupled relative thereto by an externally threaded, enlarged headed bolt 39 having lock nut 40 threaded thereon. A friction providing washer or gasket 41 may be positioned between the opposed faces of flange 36 and member portion 38a. An unthreaded central opening through portion 38a matches threaded opening 37 in flange 36, both receiving bolt 39 therethrough.

Preferably cylindrical rod or arm 42 at its inboard end has flattened, disk-like member 43. Member 43 has internally threaded opening 44 therethrough, whereby to threadably engage the externally threaded shaft of bolt 45 having nut 46 threaded on the end thereof. Bolt 45 connects members 38b and 43 to one another. A washer or gasket 47 may be interposed therebetween. Member 38b has an unthreaded opening centrally therethrough to match opening 44 in member 43.

In each of the disk-disk member facings of this invention (both forms in all figures) one of the disks has an internally threaded opening centrally therethrough, the other has an unthreaded matching central opening. The threaded bolt which engages them, with its lock nut, engages one disk and clamps the other face to face therewith.

A spring-loaded piston-piston rod extension-contraction unit generally designated 48 is interposed in the lengths of rod 42, the outboard portion thereof being designated 42a. This unit (particularly see FIG. 3) comprises a pair of hollow sleeves 49 and 50 mounted parallel to one another from a common base 51 which is attached to the outboard end of stub shaft 42. Piston rods 52 and 53 have pistons or plungers as seen at 54 on rod 52 which reciprocate within sleeves 49 and 50. Threaded, perforated plugs 55 and 56 removeably seal the ends of sleeves 49 and 50. Pistons 54 may have wear rings or o-rings circumferential thereto if desired.

Piston rods 52 and 53 are rigidly mounted parallel to one another on common base 57 to which is attached the inboard end of rod 42a. Air relief passages may be provided through base 51 at the ends of sleeves 49 and 50, if required and, additionally, through plugs 55 and 56, also if required to permit smooth, fairly easy, but air cushioned reciprocation of the pistons within sleeves 49 and 50 on rods 52 and 53. A compression spring 58 extends between recesses 59 (in base 57) and 60 (in base 51), also optionally retained by sleeve retainers 62 and 63. Thus the spring loaded piston-piston rod extension-contraction unit has a spring loading normally biased toward extension of the piston rod with respect to the piston positioned within the first arm 42, 42a.

The outboard end of rod 42a preferably has circular disk 64 thereon having internally threaded opening 64a centrally therethrough. Outboard arm 65 has inboard circular disk 66 on the inboard end thereof adapted to be put into facing relationship with disk 64, optionally with washer or gasket 67 therebetween. Disk 66 has central unthreaded opening 66a therethrough. Externally threaded bolt 67 threadably engages the disk 64 and has lock nut 68 thereon. The outboard end of arm or rod 65 is bent at right angles as at 65a and has flat disk or cylindrical plate member 69 fixed thereto.

An elongate, configured, lower side open, forearm and wrist encasing sleeve 70 (generally designated) is provided having outboardmost upper portion 70a adapted to overlie the back side of the hand proper, portion 70b overlying and clasping the outer portion of the wrist and 70c which overlies and clasps the outboard portion of the forearm adjacent the wrist. Another portion 70d partially curves under and engages the under side of the forearm. An arcuate bar 71 encircles the outer portions of the palm, short of the fingers, passing between the thumb and forefinger, as well. This arcuate bar 71 serves to brace the hand for thumb and finger action. A plurality of adjustable elastic bands 72, 73 and 74 serve to engage the inboard side of the wrist and the inboardmost portion of the forearm and center portion of the forearm respectively. Bands 72-74, inclusive are fixable to the opposed arcuate sides of the sleeve portions 70b and 70c.

Extending inboard of the inward end 70e of sleeve 70 is an angled or curved piece or member 75. This member serves as a linkage between sleeve 70 and the train of arms, joint members and pistons previously described, as will be hereinafter described. Additionally, the free ends of straps or elastic members 72-74, inclusive are removeably securable, as best seen in FIG. 2, to the opposite portions of sleeve 70 by snap fasteners, buckles or frictional engagements, such as that shown, for example, the trademarked type of engagement known as Vel-Cro, as seen at 72a-74a, inclusive.

Referring particularly to FIG. 5, which shows the articulation between rod 65 and member or flange 75, it may be seen that, fixed at right angles to the inboard end of configured flange 75 is circular disk-like member 76. Double disk member 77 has one disk 78 thereof positioned in face to face relationship with one side of disk 76 and the other disk 79 placed in abutting, face to face relationship with the outboard face of disk 69 on rod portion 65a. Central openings (not seen) are provided in disks 69 and 79, the opening in disk 79 internally threaded. Bolt 80, which is externally threaded, has lock nut 81 on the end thereof. A washer 82 may optionally be placed between disks 69 and 79.

Disk 76 has unthreaded opening 76a therethrough, centrally thereof, matching threaded central opening 78a through disk 78. Threaded bolt 83 having lock nut 84 thereon threadably engages passage 78a and penetrates passage 76a, constricting the disks 76 and 78 in face to face frictional contact through optional washer 85.

FIGS. 6-9, inclusive show the left arm device for the paired arm system seen in FIG. 2. Parts identical to those parts already described with respect to the right arm device are numbered the same in the left arm device, except primed. These parts and their relationship with one another will not again be described as they are essentially identical, but mirror images because of the difference between arms. Two changes are incorporated into the left arm device of FIGS. 6-9 inclusive, to be described.

The first difference between the showings of the left arm device and the FIGS. 1-5 showings of the right arm device comprises an arcuate motion limiting attachment at the elbow joint to prevent objectionable angular movement at the elbow joint. Thus, as seen in FIG. 1, in normal extension of the user's arm, the elbow joint at the outboard end of arm 42a and inboard end of arm 65 lies somewhat above the attachments at the shoulder and inboard end of sleeve 70. However, when the user's arms (dotted line showing of FIG. 1) is drawn toward the user and flexed or broken at the elbow, as shown, not only is the piston-piston rod extension-retraction unit compressed, but the elbow joint may reverse its angularity so the joint falls below the connections at the shoulder and sleeve inboard ends to a greater or lesser degree. This may be advantageous in certain applications and uses. However, in certain conditions of illness of certain patients, it is desirable to limit the collapsibility or reversability of the elbow joint in the direction described. In such case, the construction seen in FIGS. 6-9, inclusive is employed.

In such case, turning to these figures, the inboard end of rod 65' has, in addition to disk 66', a right angled, flanged member generally designated 86 and having relieved right angled end 86a adapted to overlay and contact, under certain conditions, the outboard portion of rod 42a, thus preventing the angling of members 42a and 65 as seen in FIG. 1 substantially reversing in the direction shown in dotted lines in FIG. 1. Member 86, being integral with disk 66 and rod 65 has a continuation of passage 66a running therethrough to receive bolt 67.

The second difference between the left and right arm devices of FIGS. 1-9 inclusive consists in the enlargement or lengthening of the extension-retraction unit 48' with respect to the overall length of arms or rods 42' and 42a'. The shoulder-elbow distance remaining the same, the length of unit 48' is proportionately increased. This gives more leeway with respect to length adjustment for users of different arm length, as well as greater range of spring controlled flexibility for many types of arm motions.

There has thus been described a structural chain of articulated members and sleeves, which include the following elements, working from the plate attachment 28:

(1) Hollow sleeve 30 adapted to removeably receive and removeably lock therewithin (by pin or pins 33 through sleeve 30):

(2) The normally vertical, preferably hollow shaft or tube 34 which is received in sleeve 30 and pinned therein against rotational movement and vertical movement;

(3) The forearm clasping and hand encircling sleeve member 70;

(4) A train of arms and articulating joints and slide means therebetween comprising:
- (a) A double element joint adjacent the shoulder of the user between shaft 34 and arm 42;
- (b) A single element joint with an optional arm limitation (member 86, 86a) at the elbow between arms 42a and 65;
- (c) A piston-piston rod extension-retraction device 48 received within the length of the first arm 42, 42a, such normally having a spring loading for extension of the piston rods with respect to said pistons (seen in FIG. 3 in detail); and
- (d) A double element joint just over the forearm past the elbow adjacent the inboard end of sleeve 70 between rod 65 and configured flange 75.

It should be noted that the optional flanged member 86, 86a between rods 65 and 42a not only operates to prevent reversal of the joint as previously described, but also prevents over-extension of the elbow joint by the user in the arm extended position of FIG. 1 (full lines).

A double element joint, as above described, comprises two closely adjacent, right angle oriented sets of pinned, sliding, circular plates which, together, as a functioning unit, operate to permit multi-dimensional and multi-planar movement. A single element joint is one such set with movement limited to a single special plane.

As specific examples of the foregoing, the double element joint at the top of normally vertical shaft 34 involving disks 36-38a and 38b-43 permits full, three dimensional, shoulder articulation. The single element joint at the elbow between rods 42a and 65, involving disks 64 and 66 and optional flanged element 86, 86a, together with the piston-piston rod extension-retraction assembly, permits flexion and extension of the forearm with respect to the elbow and upper arm (with optional extension limitation thereof in both directions). The outermost double element joint, between rod 65 and flange 75, involving disks 69-82 and 76-78, permits pronation and supination of the forearm with respect to the upper arm and elbow joint of the user. Given the double element joints at the shoulder and base of sleeve 70, the planar flexion of the elbow permitted by the single element joint at the elbow with the extension-retraction assembly is sufficient for the full range of motion of the arm.

The provision of the circular or disk-like elements in the said joints, with the threading of one of the disk-like elements and optional washer, together with a lock nut, permit a graded, fixed tightening or tension at each joint which provides a variable (yet fixed for each given setting) frictional loading at each joint element. These frictional loadings at each joint element, which may be different from joint connection to joint connection, operate, jointly and severally, in conjunction with the spring loading in the extension-retraction assembly, to damp the muscular spasms and neuro-muscular oscillations of the user which, in spastic paralysis, are involuntary and unwilled. The variable (yet fixed at a given setting) resistance provided at each joint, or with the spring resistance in the extension-retraction assembly, permits the entire train of joint elements, jointly and severally, to be uniquely and variably settable or adjustable for a given individual's problems. Different spring strengths originally inserted in the extension-retraction assembly will give different resistance as required for arm flexion and extension.

The desired frictional engagement for a given joint element connection (bolt through two facing disk elements) is accomplished by tightening down the bolt engagement of each of the joint element facing sets to the desired tension, with the lock nuts on the free end of the bolt fixing the setting at that tension for each such joint element.

The instant device or apparatus thus comprises a neuromuscular stabilizing device for the human arm and hand which comprises, in combination: (1) A normally vertical support post or arm 34 having normally upper and lower ends, (2) a sleeve adapted to a embrace a human forearm which has an inboard end (toward the elbow) and an outboard end (toward the hand) and (3) an articulated linkage chain which couples together the upper end of the support post and the inboard end of the sleeve. The articulated linkage chain includes arms 42, 42a and 65, a double element joint at the shoulder, the piston-piston rod extension-retraction assembly 48 in arm 42, 42a, a single element elbow joint between arms 42a and 65 with optional arcuate motion limitation means, and a double element joint at the outboard end of rod 65 which couples to the sleeve through flange 75.

Each of the joint elements described includes a pair of disk-like or circular facing elements having each a central hole therethrough, with one of the circular facing elements having the hole therethrough internally threaded. A threaded bolt engages the two circular facing elements and is threaded into the said one element, with a lock nut threaded on the free end of the bolt. A frictional washer may be provided between the pair of circular or disk-like facing elements.

USE AND APPLICATION

As previously mentioned, the subject device may be mounted, in single or dual arm application, on a chair, a wheel chair, a vertical standing frame or on a body harness. All that is needed is an essentially vertical mounting of one or more plates 28 on such a chair back, frame, body harness or the like, immediately outside the position of the shoulder joints of the individual and therebelow, whereby the tops of the shafts 34 and 34' will be at or opposite the top of the shoulder level of the individual when he is sitting in the chair, standing within the work frame or has the body harness mounted on him.

It is desireable that, when the device is fitted to the user's arm, with the forearm in the sleeve and the hand grasping the bar 71, the arrangement of the parts will be substantially as seen in FIG. 1, specifically, that is, with the piston rod substantially fully extended from sleeves 49 and 50 and there being a slight upward angle between arms 42a and 65 at the elbow joint. Depending on the length of sleeves 49 and 50 and piston rods 52 and 53, a certain amount of length adjustment may be taken up in the extension-retraction assembly with the device sized for quite long arms at full piston extension and partial retraction for shorter arms. Alternatively, either rod 42 or rod 42a, or both of them, may be supplied in different lengths threadably engagable with base 51 and 57, respectively, so different length segments can be substituted in the device (not shown).

Depending upon the disability pattern (types, amplitudes, distributions and magnitudes of tremoring) in the individual, the train of joints is adjusted to provide the desired resistance at each element. This may be readjusted, from time to time, as changes take place in the nervous system of the individual from regaining control or as fatigue sets in, as muscular development occurs from use, as learning and skill are achieved, etc.

Before the forearm, wrist and hand are engaged or disengaged, the straps 72-74, inclusive are unsnapped or disengaged, to be engaged at the desired tension, once the hand, wrist and forearm are inserted into the sleeve and hand engaging structure.

FIGS. 10-15, INCLUSIVE

This variation or modification of the subject improvement is directed to a device which incorporates an extra arm and joint in the linkage train between the base post and forearm encircling sleeve. The purpose of such inclusion is to obtain greater restrictive control of the range and ease of both flexion and extension of the forearm with respect to the upper arm, while utilizing a piston-piston rod extension-retraction assembly to achieve and permit fitting variation and spring resisted flexion of the forearm with respect to the upper arm.

In this modification, surveying the structure, there is a base post 100 at the top of which is a double element joint broadly designated 101. A piston-piston rod extension-retraction assembly generally designated 102 is received in the length of the first rod. A single element joint 103, generally designated, joins the first rod and a second rod, the latter having, at its outboard end, another single element friction joint 104, in this case preferably with extension limiting means to be described. A third arm or rod extends out of joint 104, leading to a second double element joint 105 which connects to an angled flange secured to a forearm sleeve construction. The first arm 106 has inboard and outboard portions 106a and b. The second arm 107 connects segment 106b and third arm 108. Flange 109 connects to arm 108 through double element joint 105 on the inboard side and to sleeve 110 on the outboard side.

Tracing the linkage and joint elements in more detail, from the inboard end at tube or rod 100, it is first noted that a mounting for tube 100 is provided as seen in the lower left hand corner of FIG. 1, here not illustrated. The upper end of rod 100 has rounded right angle flange 111 thereon. Paired right angle disk member 112 has inboard disk 112a coupled with flange 111 by bolt 113 having lock nut 114 thereon. Outboard disk 112b abuts against disk member 115 on the inboard end of rod 106 through an optional washer. Bolt 116 having lock nut 117 thereon engages disks 112b and 115 through central openings therethrough, one of which is threaded, the other unthreaded. One of flange 111 and disk 112a has the central opening therethrough threaded for engagement by bolt 113.

The piston-piston rod assembly 102 has inboard base 118 to which are attached hollow sleeves 119 and 120. Piston rods 121 and 122 are fixed at their outboard ends to base 123 and have plungers or pistons (unseen) within sleeves 119 and 120. Air relief openings are provided as required at each end of the sleeves. Compression spring 124 extends between bases 118 and 123 and biases the assembly toward the open position seen. The construction of this assembly is the same as seen in FIG. 3.

At the joint between rods 106b and 107, perforated disk 125 on rod 106b is faced by perforated disk 126 on rod 107. The passage or opening through one of disks 125 and 126 is internally threaded, the other not. Threaded bolt 127 having lock nut 128 thereon joins the disks 125 and 126 in face to face sliding relationship, optionally with a washer therebetween.

Rod 107 has centrally perforated circular disk 129 thereon, opposed by centrally perforated disk 130 on rod 108. Right angle flange member 131 having relieved end 131a is also integral with rod 108, with relieved end 131a overlying the outboard end of rod 107. One of the passages through disks 129 or 130 is internally threaded. The passage through disk 130 also extends through member 131. Threaded bolt 132 joins disks 129 and 130 and has lock nut 133 thereon.

On the right angled end 108a of rod 108 is fixed circular, centrally perforated disk 134. Double disk member 135 has upper disk 135a, centrally perforated, facing disk 134. Bolt 137, receiving lock nut 138 thereon, is threaded, threadably engaging that one of the two passages through disks 134 and 135a which is threaded. A washer may be employed between disks 134 and 135a as between 129 and 130. Lower disk 135b, centrally perforated, is held in facing relationship with centrally perforated disk 139 fixed to strap or member 109. Bolt 140, with lock nut 141 thereon, engages the passages through disk 135b and 139, one of them threadably, with an optional washer therebetween.

In the views of FIGS. 10 and 11, the shoulder area of the user's right arm is seen at 142, the upper arm at 143, elbow at 144, forearm at 145, wrist at 146 and hand 147. Sleeve 110 has outboard end 110a, wrist covering zone 110b, forearm overlying portion 110c and forearm cupping underportion 110d with inboard end 110e. Bar 147a encircles the hand before the fingers and after the thumb. Straps 148, 149 and 150 loop under the wrist and forearm of the user and, in the example shown, have Vel-Cro connection patches 148a–150a, respectively, on sleeve portion 110d for removeable securement.

With respect to this modification or variation, there has been described an entire structural chain of articulated members, a sleeve, an extension-retraction assembly and joints, which includes the followng elements, working from an unshown, yet assumed, plate attachment and sleeve mounting like that seen in FIG. 1. (In the view of FIG. 11, a plate 151 is shown secured by rivets 152 to an upright member 153 having a base 154. A like typical support construction is seen in FIG. 2 with plate 28 attached to vertical member 90 having base 91.)

(1) The normally vertical shaft 100 typically received within a sleeve (unseen) like sleeve 30 of FIG. 1 and pinned therein against rotational movement and vertical movement;

(2) The forearm clasping and hand encircling sleeve member 110;

(3) A train of arm, articulating joints therebetween, and an extension-retraction assembly comprising;

(a) A double element joint 101 adjacent the shoulder of the user between rod 100 and arm 106a;

(b) A first single element joint 103 between the shoulder and elbow linking rods 106b and 107;

(c) A second single element joint 104 with an arm limitation (member 131, 131a against excessive elbow extension) at the elbow coupling rods 107 and 108;

(d) A double element joint 105 just over the forearm past the elbow adjacent the inboard end of sleeve 110 linking rod 108 and flange 109; and (e) The extension-retraction assembly 102 received within arm 106 and between double element joint 101 and single element joint 103.

The nature of double and single element joints has previously been described in detail with respect to the structure of FIGS. 1–9, inclusive and will not be repeated. In this array, the double element joint 101 at the user's shoulder again permits shoulder articulation in three dimensions. The two, intermediate, single element joints 103 and 104, together with the extension-retraction assembly 102, permit flexion and extension of the forearm with respect to the upper arm and elbow (with extension limitation thereof by member 131, 131a). The outermost double element joint, between rod 108 and flange 109, permits pronation and supination of the forearm with respect to the elbow and upper arm of the user.

The description of the user of the circular or disk-like elements at the joints, with the threading of one of the disk-like elements, optional use of a washer, and a bolt with a lock nut, to permit a graded, fixable tension at each joint providing a variable (yet fixed for a given setting) friction loading at each joint element will not be repeared as it is the same as previously described with respect to FIGS. 1–9, inclusive.

This specific form of stabilizing device comprises, then, in combination: (1) a normally vertical support post or arm 100 having upper and lower end thereto, (2) a sleeve adapted to embrace the human forearm having an inboard end toward the elbow and an outboard end towards the hand and (3) an articulated linkage chain which couples together the upper end of the support post and the inboard end of the sleeve. This articulated linkage chain includes the following elements. A first arm 106 has inboard and outboard ends and a piston-piston rod extension-retraction unit received therewithin. Arm 106 is connected to the upper end of post 100 via or through a double element friction joint. Second arm 107 is coupled at its inboard end to the outboard 106b of arm 106 by a single element friction joint. A third arm 108 is coupled at its inboard end to the outboard end of second arm 107 through a second single element friction joint 104, the latter also having extension limiting means in one direction, member 131, 131a. The outboard end of third arm 108 is coupled to sleeve 110 via flange 109 through a double element friction joint 105.

Looking at FIG. 10, the user's arm is about two-thirds extended. Further extension of the arm, particularly with a right angled supination from the position seen is possible, but complete extension, and particularly over-extension at the elbow is limited by member 131, 131a. The extension from the position shown in FIG. 10 would be through both the extension-retraction unit 102 (assuming some extension still existing in the position shown) and joints 103 and 104.

In contraction of the user's arm from the position of FIGS. 10 and 11, with or without supination from the position shown, the extension-retraction assembly condenses or telescopes against compression spring 124. Further, there is action at joints 103 and 104 with arm 107 moving counterclockwise around joint 103 and arm 108 moving clockwise around joint 104 (with or without action at the upper joint, which depends upon whether the arm was raised or lowered in the given action). However, in the construction of FIGS. 10-15, inclusive, joint 104 remains above the inboard end of rod 107 and outboard end of rod 108 at all times.

With the exception of the previous description, the description of operation, use and application of the device of FIGS. 10-15 inclusive is the same as with respect to FIGS. 1-9, inclusive.

From the foregoing, it will be seen that this invention is one well adapted to attain all of the ends and objects hereinabove set forth together with other advantages which are obvious and which are inherent to the apparatus.

It will be understood that certain features and sub-combinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

We claim:

1. A neuro-muscular stabilizing device for a human arm comprising, in combination:
   a normally vertical post having normally upper and lower ends,
   an elongate, substantially rigid sleeve adapted to embrace a human forearm having an inboard end (towards the elbow) and an outboard end (toward the hand),
   a coupling linkage train connecting the upper end of the post and the inboard end of said sleeve, comprising:
   (a) a first arm having inboard and outboard ends connected to the upper end of the post at its inboard end,
   (b) the means connecting said post and the inboard end of said first arm comprising a double element friction joint,
   (c) another arm having inboard and outboard ends coupled at its outboard end to the inboard end of the sleeve,
   (b) the means coupling the outboard end of said other arm and the inboard end of the sleeve comprising a double element friction joint,
   (e) means coupling the inboard end of the other arm and the outboard end of the first arm to one another comprising a single element friction joint, and
   (f) a cylinder-piston rod extension-retraction assembly received within the first arm and forming an extendable and retractable part thereof, said assembly having a spring loading for extension of the piston rod with respect to said cylinder,
   (g) the piston part of the said assembly fixed to one part of said arm and the rod part of the assembly fixed to another part thereof, so that insertion of the rod part of the assembly into the cylinder part shortens the said first arm and extension thereof lengthens the said first arm,
   (h) the sleeve and arm lengths so sized, with the extension-retraction assembly fully extended, so that the means coupling the inboard end of the other arm and the outboard end of the first arm to one another normally is located substantially at the elbow of a user of the device when the user's arm, engaged, with the device, is fully extended.

2. A device as in claim 1 wherein each joint element includes a pair of circular facing elements having each a central hole therethrough, one of the circular facing elements having the hole therethrough internally threaded,
   a threaded bolt engaging the two circular facing elements and threaded into the said one element, and
   a lock nut threaded on the end of the bolt.

3. A device as in claim 1 including an extension limiting means in one direction on the single element friction joint coupling the said first arm to the said other arm comprising a plate fixed to the inboard end of the other arm which has a portion thereof overlying the outboard end of the said first arm.

4. A device as in claim 1 including socket means receiving said normally vertical post and means for fixing said normally vertical post in said socket.

5. A device as in claim 1 wherein the extension-contraction assembly employs a pair of cylinder and piston rod units in parallel array.

6. A device as in claim 1 wherein the extension-retraction assembly comprises substantially the entire portion of the length of the first arm.

7. A device as in claim 1 wherein the extension-retraction assembly comprises only a part of the length of said first arm.

* * * * *